United States Patent
Chen

(10) Patent No.: US 7,203,272 B2
(45) Date of Patent: Apr. 10, 2007

(54) CONE-BEAM FILTERED BACKPROJECTION IMAGE RECONSTRUCTION METHOD FOR SHORT TRAJECTORIES

(75) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/286,527

(22) Filed: Nov. 23, 2005

(65) Prior Publication Data

US 2006/0115040 A1    Jun. 1, 2006

Related U.S. Application Data

(60) Provisional application No. 60/630,919, filed on Nov. 24, 2004.

(51) Int. Cl.
G01N 23/00 (2006.01)
(52) U.S. Cl. .................................................. 378/19
(58) Field of Classification Search .................. 378/4, 378/15–20, 901
See application file for complete search history.

(56) References Cited

U.S. PATENT DOCUMENTS

| 5,881,123 | A  * | 3/1999 | Tam ............................ 378/4 |
| 6,084,937 | A  * | 7/2000 | Tam et al. ................... 378/4 |
| 6,292,525 | B1 * | 9/2001 | Tam ............................ 378/4 |
| 6,504,892 | B1   | 1/2003 | Ning ........................... 378/4 |
| 6,574,297 | B2 * | 6/2003 | Tam ........................... 378/15 |
| 2003/0072406 | A1 | 4/2003 | Yang ........................... 378/4 |
| 2003/0161444 | A1 | 8/2003 | Katsevich ................. 378/210 |
| 2004/0086074 | A1 | 5/2004 | Taouchi ....................... 378/4 |
| 2005/0047542 | A1 * | 3/2005 | Chen .......................... 378/19 |
| 2006/0067457 | A1 * | 3/2006 | Zamyatin et al. ........... 378/4 |

OTHER PUBLICATIONS

Yu et al., Feldkamp-type VOI reconstruction from super-short-scan cone-beam data, Med. Phys., vol. 31, No. 6, Jun. 2004.*
Kudo et al., New Super-Short-Scan Algorithms for Fan-Beam and Cone-Beam Reconstruction, IEEE, 2003.*
L.A. Feldkamp et al; Practical Cone Beam Algorithm, J. Opt. Soc. Am. A 1, 612-619(1984).
G. Wang, A General Cone-beam Reconstruction Algorithm, IEEE Trans. Med. Imaging 12, 486-496 (1993).
A. Katsevich, Theoretically Exact Filtered Backprojection-type Inversion Algorithm For Spiral CT, SIAM (Soc. Ind. Appl. Math.) J. Appl. Math. 62, 2012-2026 (2002).
Tingliang Zhuang, et al., "Fan-beam and cone-beam image reconstruction via filtering the backprojection image of differentiated projection data; Fan-Beam and cone-beam image reconstruction via filtering the backprojection image", Physics in Medicine and Biology, Taylor and Francis Ltd. London, GB, vol. 49, No. 24, Dec. 21, 2004.

(Continued)

*Primary Examiner*—Courtney Thomas
*Assistant Examiner*—Alexander Taningco
(74) *Attorney, Agent, or Firm*—Quarles & Brady LLP

(57) ABSTRACT

An image reconstruction method for cone beam x-ray attenuation data acquired over a super-short-scan, short-scan or full-scan includes backproejcting over three adjacent segments of the arc traversed by the x-ray source. Each backprojection consists of a weighted combination of 1D Hilbert filtering of the modified cone-beam data along both horizontal and non-horizontal directions.

11 Claims, 10 Drawing Sheets

OTHER PUBLICATIONS

Tingliang Zhuang, et al., "Image reconstruction via filtered backprojection for cone-beam data from two orthogonal circles using an equal weighting scheme".

Alexander Katsevich, "A general scheme for constructing inversion algorithms for cone beam CT", International Journal of Mathematics and Mathematical Sciences, vol. 2003, No. 21, 2003.

Yu Zou et al., "Exact image reconstruction on PI-Lines from minimum data in helical cone-beam CT", Physics in Medicine and Biology, Taylor and Francis Ltd., London, GB, vol. 49, No. 6, Mar. 21, 2004.

Lauritsch G. et al., "Exact consideration of data redundancies for spiral cone-beam CT", Proceedings of the Spie—The International Society for Optical Engineering, Medical Imaging 2004, Image Processing, vol. 5370, No. 1, Feb. 19, 2004, San Diego, CA.

Kudo, et al., "Extended cone-beam reconstruction using Radon transform", Nuclear Science Symposium 1996, Conference Record., 1996 IEEE Anaheim, CA Nov. 2-9, 1996. New York, NY, vol. 3, Nov. 2, 2006.

Noo et al., "Image reconstruction from fan-beam projectionson less than a short scan", Physics in Medicine and Biology, Taylor and Francis Ltd., London, GB, vol. 47, No. 14, JUl. 21, 2002.

Hengyong Yu, et al., Feldkamp-type VOI reconstruction from super-short-scan cone-beam data, Med. Phys. 31, (6) Jun. 1004.

Hiroyuki Kudo, et al., New Super-Short-Scan Algorithms for Fan-Beam and Cone-Beam Reconstruction, 2003 IEEE.

\* cited by examiner

CONE-BEAM FILTERED BACKPROJECTION IMAGE RECONSTRUCTION METHOD FOR SHORT TRAJECTORIES

CROSS-REFERENCE TO RELATED APPLICATIONS

This application is based on U.S. Provisional Patent Application Ser. No. 60/630,919 filed on Nov. 24, 2004 and entitled "CONE-BEAM FILTERED BACKPROJECTION IMAGE RECONSTRUCTION METHOD FOR SHORT TRAJECTORIES."

STATEMENT REGARDING FEDERALLY SPONSORED RESEARCH

This invention was made with government support under Grant No. CA109992 and EB001683 awarded by the National Institute of Health. The United States Government has certain rights in this invention

BACKGROUND OF THE INVENTION

The present invention relates to computed tomography (CT) imaging apparatus; and more particularly, to a method for reconstructing images from divergent beams of acquired image data.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, shape of the x-ray beam, and detector system.

As shown in FIG. 1, the first generation utilized a single pencil x-ray beam and a single scintillation crystal-photomultiplier tube detector for each tomographic slice. After a single linear motion or traversal of the x-ray tube and detector, during which time 160 separate x-ray attenuation or detector readings are typically taken, the x-ray tube and detector are rotated through 1° and another linear scan is performed to acquire another view. This is repeated typically to acquire 180 views.

A second generation of devices developed to shorten the scanning times by gathering data more quickly is shown in FIG. 2. In these units a modified fan beam in which anywhere from three to 52 individual collimated x-ray beams and an equal number of detectors are used. Individual beams resemble the single beam of a first generation scanner. However, a collection of from three to 52 of these beams contiguous to one another allows multiple adjacent cores of tissue to be examined simultaneously. The configuration of these contiguous cores of tissue resembles a fan, with the thickness of the fan material determined by the collimation of the beam and in turn determining the slice thickness. Because of the angular difference of each beam relative to the others, several different angular views through the body slice are being examined simultaneously. Superimposed on this is a linear translation or scan of the x-ray tube and detectors through the body slice. Thus, at the end of a single translational scan, during which time 160 readings may be made by each detector, the total number of readings obtained is equal to the number of detectors times 160. The increment of angular rotation between views can be significantly larger than with a first generation unit, up to as much as 36°. Thus, the number of distinct rotations of the scanning apparatus can be significantly reduced, with a coincidental reduction in scanning time. By gathering more data per translation, fewer translations are needed.

To obtain even faster scanning times it is necessary to eliminate the complex translational-rotational motion of the first two generations. As shown in FIG. 3, third generation scanners therefore use a much wider fan beam. In fact, the angle of the beam may be wide enough to encompass most or all of an entire patient section without the need for a linear translation of the x-ray tube and detectors. As in the first two generations, the detectors, now in the form of a large array, are rigidly aligned relative to the x-ray beam, and there are no translational motions at all. The tube and detector array are synchronously rotated about the patient through an angle of 180–360°. Thus, there is only one type of motion, allowing a much faster scanning time to be achieved. After one rotation, a single tomographic section is obtained.

Fourth generation scanners feature a wide fan beam similar to the third generation CT system as shown in FIG. 4. As before, the x-ray tube rotates through 360° without having to make any translational motion. However, unlike in the other scanners, the detectors are not aligned rigidly relative to the x-ray beam. In this system only the x-ray tube rotates. A large ring of detectors are fixed in an outer circle in the scanning plane. The necessity of rotating only the tube, but not the detectors, allows faster scan time.

Divergent fan-beam scanning modes have the potential to allow fast data acquisition. But image reconstruction from divergent-beam projections poses a challenge. In particular, the projection-slice theorem is not directly applicable to the divergent-beam projections since the shift-invariance in a single view of projections is lost in the divergent-beam case. One way to bypass this problem is to explicitly rebin the measured divergent-beam projections into parallel beam projections. This is the basic method currently used in solving the problem of fan-beam image reconstruction. After the rebinning process, one can take the advantages of the fast Fourier transforms (FFT) to efficiently reconstruct images.

Recently, the divergent cone-beam reconstruction problem in x-ray CT has attracted increased attention due to the rapid development of multi-row detectors. In the cone-beam case, it is much more complicated to rebin cone-beam projections into parallel-beam projections. The huge cone-beam data set also poses a big challenge to the potential data storage during the rebinning process. The main stream of the developments in cone-beam reconstruction has been focused on the development of approximate or exact reconstruction methods. For circular-based source trajectories, methods disclosed by L. A. Feldkamp, L. C. Davis, and J. W. Kress, "Practical Cone Beam Algorithm," J. Opt. Soc. Am. A 1, 612–619(1984); G. Wang, T. H. Lin, P. Cheng, and D. M. Shinozaki, "A general cone-beam reconstruction algorithm," IEEE Trans. Med. Imaging 12, 486–496 (1993); generate acceptable image quality up to moderate cone angles (up to 10° or so). Exact reconstruction algorithms have also been proposed and further developed for both helical source trajectory and more general source trajectories. Most recently, a mathematically exact and shift-invariant FBP reconstruction formula was proposed for the helicauspiral source trajectory A. Katsevich, "Theoretically exact filtered backprojection-type inversion algorithm for spiral CT," SIAM (Soc. Ind. Appl. Math.) J. Appl. Math. 62, 2012–2026 (2002).

There are two types of analytic cone-beam reconstruction algorithms: exact and approximate. The first and most practical approximate cone-beam reconstruction algorithm was proposed by Feldkamp, Davis and Kress (FDK) for a circular x-ray source trajectory. It is a heuristic extension of standard fan-beam reconstruction to the cone-beam case by introducing a "cosine" factor. Extensions to this approximate algorithm have been developed. Due to its one-dimensional shift invariant filtering kernel it has been applied to various medical imaging systems. The original FDK algorithm is applied to a complete circular scanning path. Recently, the fan-beam super-short-scan FBP reconstruction formulae has been extended to the cone-beam case to obtain super-short-scan FDK-type algorithms.

There is an alternative method to obtain an approximate cone-beam reconstruction algorithm; namely, apply a mathematically exact algorithm to an incomplete source trajectory. In the case of a single arc used to reconstruct a 3D volume the data is incomplete according to Tuy's data sufficiency condition. The problem has been addressed in the Grangeat framework using a shift variant filtered backprojection reconstruction formula. When a rebinning scheme is introduced, a short scan image reconstruction algorithm in the Grageat framework results.

Recently, a general procedure to generate shift-invariant cone-beam reconstruction algorithms has been developed for a general source trajectory provided that the data sufficiency condition is fulfilled. There is a need for such an image reconstruction method where the data sufficiency condition has not been met.

SUMMARY OF THE INVENTION

The present invention is a new cone-beam FBP reconstruction method in which a shift-invariant FBP algorithm is applied to an arc scanning path. The scanning path may be a full circle (full-scan), an arc satisfying the short scan condition (short-scan), viz, the angular range of the scanning path is π+ fan angle, or an arc with a shorter scanning path (super-short-scan), viz., the angular range of the scanning path is less than the above short scan condition. The resulting method is not mathematically exact; however, the shift-invariant feature is preserved. The method includes backprojections from three adjacent segments of the arc defined by $T_1(\vec{x})$, $T_2(\vec{x})$ and $T_3(\vec{x})$. Each backprojection step consists a weighted combination of 1D Hilbert filtering of the modified cone-beam data along both horizontal and non-horizontal directions. The redundant projections were equally weighted to achieve the optimal noise variance.

GENERAL DESCRIPTION OF THE INVENTION

In the following discussion a third-generation cone-beam source-detector configuration is assumed where the detector is constantly opposed to the source. The coordinate system and the parameters used herein are demonstrated graphically in FIG. 8. Letter O labels the iso-center of rotation. The coordinate system x-y-z located at O is the laboratory Cartesian coordinate system, and the z axis is the axis about which the detector and source rotate. The detector plane is perpendicular to the iso-ray originating from the source point $\vec{y}(t)$. The distance along the iso-ray between the source and detector is D. In the laboratory coordinate system, the point $\vec{x}$ within the object is written as $\vec{x} = (x,y,z)$. The density of a 3D object to be reconstructed is denoted as $f(\vec{x})$. The cone-beam projection of the object from the source point $\vec{y}(t)$ in the direction $\hat{r}$ is written as:

$$g(\hat{r},t) = \int_o^\infty ds\, f[\vec{y}(t) + s\hat{r}] \quad (1)$$

Figure 9:
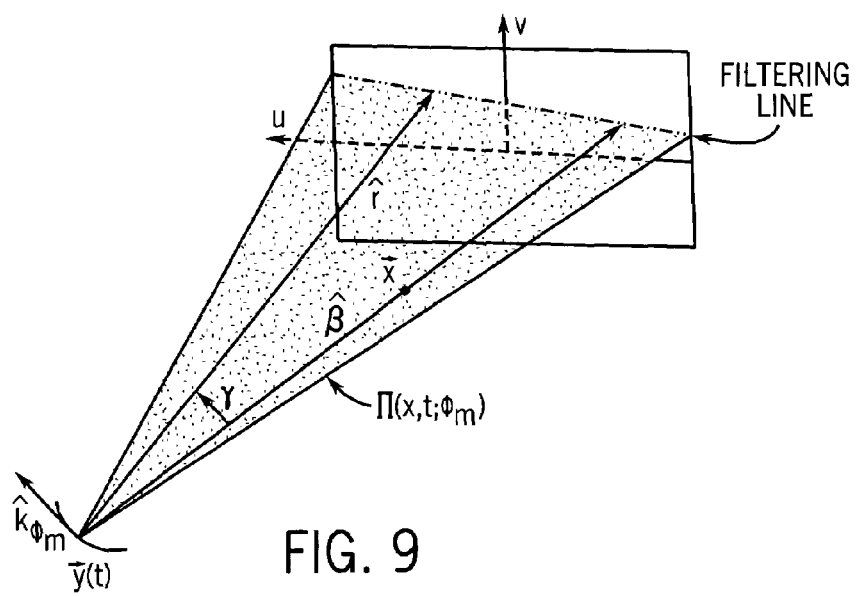
FIG. 9 is another pictorial representation of parameters used to derive the equations for the present invention.

A unit vector $\hat{\beta}$ will be defined in the direction from a source point $\vec{y}(t)$ to an object point $\vec{x}$.

$$\hat{\beta} = \frac{\vec{x} - \vec{y}(t)}{|\vec{x} - \vec{y}(t)|} = (\cos\beta \sin\alpha, \sin\beta \sin\alpha, \cos\alpha), \quad (2)$$

where $\beta$ and $\alpha$ are the longitudinal and azimuthal angles respectively. We next introduce a plane which contains the vector $\hat{\beta}$, and which is characterized by its normal vector $\hat{k}_\phi$. In a local coordinate system this normal vector may be locally parameterized by an angle $\phi$. This plane will be denoted as $\Pi(\vec{x}, t; \phi)$ and may be written as:

$$\hat{r}(\gamma, \phi) = \hat{\beta} \cos\gamma + \hat{\beta} \times \hat{k}_\phi \sin\gamma, \gamma \in [-\pi, \pi], \quad (3)$$

where $\gamma$ is the angle measured from $\hat{\beta}$ to $\hat{r}$ as shown in FIG. 9.

The shift-invariant FBP cone-beam reconstruction formula for a general source trajectory that fulfills the data sufficiency condition (H. K. Tuy, "An inverse formula for cone-beam reconstruction," *SIAM J. Appl. Math* 43, pp. 546–552, 1983.) is given by:

$$f(\vec{x}) = -\frac{1}{4\pi^2} \sum_m \int d\gamma \frac{c_m(\vec{x}, t)}{|\vec{x} - \vec{y}(t)|} \int_{-\pi}^{\pi} d\gamma \frac{1}{\sin\gamma} \frac{\partial}{\partial q} g[\hat{r}(\gamma, \phi_m), \vec{y}(q)] \bigg|_{q=t}, \quad (4)$$

with $\phi_m \in [0, \pi)$, [A. Katsevich, "A general scheme for constructing inversion algorithms for cone-beam CT," *Int. J Math. Sci.* 21, pp. 1305–1321, 2003 and G. H. Chen, "An alternative derivation of Katsevich's cone-beam reconstruction formula," *Med. Phys.* 30, pp. 3217–3226, 2003.] and where $c_m(\vec{x}, t)$ is termed the structure factor and is explicitly dependent on the source trajectory and the selected weighting function. Thus, one may summarize the steps necessary to reconstruct a single point as: 1) Extract the measured projection data from the desired planes $\Pi(\vec{x}, t; \phi_m)$ which will be referred to as the critical planes and will be defined below, 2) Differentiate the projection data with respect to the source parameter, 3) Perform a one-dimensional filtering operation, 4) Sum the contributions over the weighted critical planes, 5) Perform a distance weighted backprojection. Thus, in deriving a reconstruction algorithm for any given trajectory the crucial step is to find and weight these critical planes.

The structure factor is calculated as follows:

$$c_m(\vec{x}, t) = sgn[\hat{k}_\phi \cdot \vec{y}(t)] \omega[\vec{x}, \hat{k}_\phi; t] \bigg|_{\phi=\phi_m-\epsilon}^{\phi=\phi_m+\epsilon}, \quad (5)$$

where at $\phi_m$ either the function $sgn[\hat{k}_\phi \cdot \vec{y}(t)]$ or the weighting function $\omega[\vec{x}, \hat{k}_\phi; t]$ as a function of $\phi$ is discontinuous. When a discontinuity occurs in either of these functions the plane $\Pi(\vec{x}, t; \phi)$ will be referred to as a critical plane. It is important to note that to reconstruct the density of a given image point, for each view angle, only the cone-beam projection data lying in these critical planes is necessary.

Since the structure factor is highly dependent upon the selected weighting function we will also review here the conditions imposed on the weighting function. The weighting function properly accounts for data redundancy, i.e., for a given image point there may be multiple intersections between the plane $\Pi(\vec{x}, t; \phi)$ and the source trajectory (i.e., $\hat{k}_\phi \cdot [\vec{x} - \vec{y}(t)] = 0$). Obviously, the weighting function must be properly normalized, $$\sum_i \omega[\vec{x}, \hat{k}_\phi; t] = 1. \quad (6)$$

To obtain the above reconstruction formula, a necessary condition on the weighting function must be imposed $$\frac{\partial}{\partial \phi} \omega(\vec{x}, \hat{k}; t) = 0. \quad (7)$$

Namely, that the weighting function must be piecewise constant with respect to the angle of rotation, $\phi$, of the plane $\Pi(\vec{x}, t; \phi)$ about $\hat{\beta}$. There are many possible weighting functions which satisfy both Eq. (6) and Eq. (7). In this work we have selected an equal weighting function which is desirable in medical CT since equal weighting is optimal for dose utilization. The equal weighting function which satisfies the conditions expressed in Eq. (6) and Eq. (7) is given as $$\omega[\vec{x}, \hat{k}_\phi; t] = \frac{1}{N}, \quad (8)$$

where N is the number of intersection points between plane $\Pi(\vec{x}, t; \phi)$ and the source trajectory.

Up to this point, we have described the exact cone-beam FBP type framework for a complete source trajectory. In the following discussion, this is extended to develop an image reconstruction method for a single arc source trajectory.

An arc source trajectory with radius R can be parameterized by the view angle variable t. thus, the position of any given view angle on the source trajectory will be given by $$\vec{y}(t) = R(\cos t, \sin t, 0), t \in [t_i, t_f], \quad (9)$$

where $t_i$ and $t_f$ are the parameters for the two ending points of the arc. The source-to-detector distance has been assumed to be twice the gantry radius, D=2R.

Figure 8:
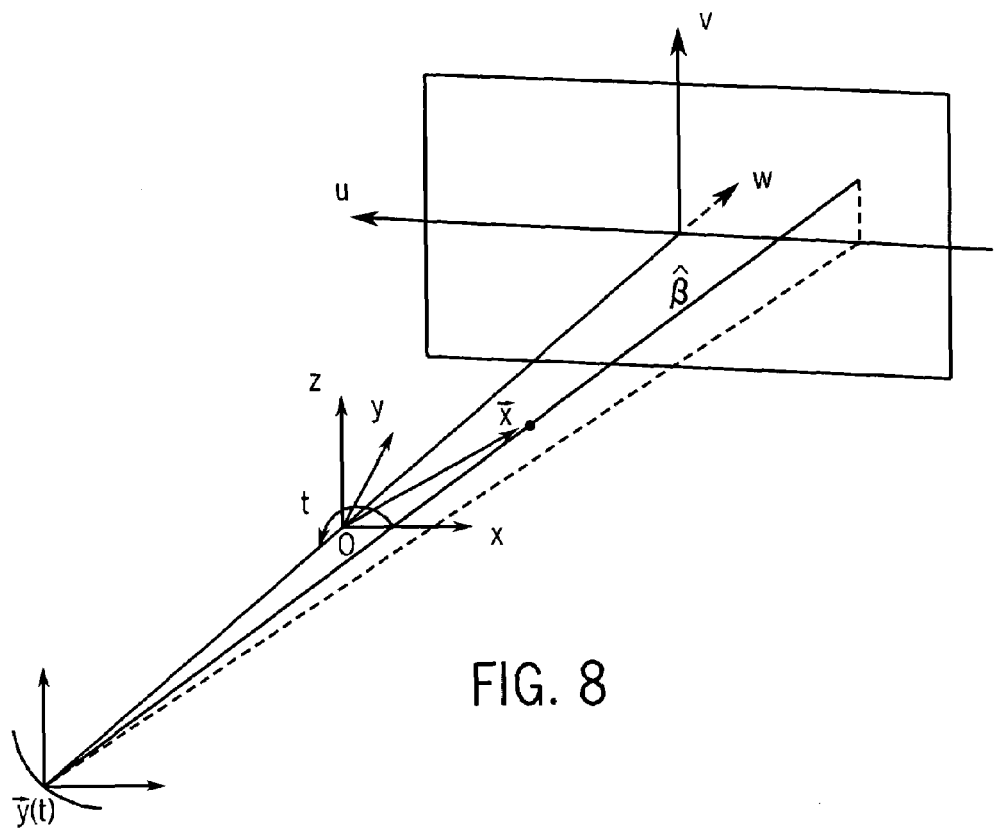
FIG. 8 is a pictorial representation of the coordinate system used to derive the equations for the present invention.

In the geometrical setup introduced above and shown in FIG. 8, the detector plane is always perpendicular to the iso-ray. The analysis presented here assumes a flat equispaced detector, however a similar analysis may be conducted for a curved equi-angular detector. For convenience we define the following rotating system:

$$\hat{\omega} = (-\cos t, -\sin t, 0), \hat{u} = (\sin t, -\cos t, 0), \hat{v} = (0, 0, 1).$$

The origin of the detector coordinate system is specified by the piercing point of the iso-ray onto the detector plane. The native detector coordinates u, v which are the signed dis tance along the directions $\hat{u}$, $\hat{v}$ respectively, will be introduced, $$u = D\frac{\hat{r}\cdot\hat{u}}{\hat{r}\cdot\hat{\omega}}, v = D\frac{\hat{r}\cdot\hat{v}}{\hat{r}\cdot\hat{\omega}}. \quad (10)$$

The derivative $$\frac{\partial}{\partial_q}$$

can be re-expressed using the chain rule of differentiation:

$$\frac{\partial}{\partial_q}g[\hat{r},\vec{y}(q)]\bigg|_{q=t} = \left(-\frac{D^2+u^2}{D}\frac{\partial}{\partial u} - \frac{uv}{D}\frac{\partial}{\partial v} + \frac{\partial}{\partial t}\right)g(u,v,t).$$

By specifying the unit vector $\hat{\beta}$ as one specific $\hat{r}$ in this native geometry, i.e., substituting the previous expression for $\hat{\beta}$ (Eq. (2)) into Eq. (10) one may obtain the cone-beam projection of the image point onto the detector, as given below:

$$u_\beta(t) = D\frac{x\sin t - y\cos t}{\frac{D}{2} - x\cos t - y\sin t}, v_\beta(t) = D\frac{z}{\frac{D}{2} - x\cos t - y\sin t}. \quad (11)$$

The detector position of the cone-beam projection of each image point from each view angle as given by $u_\beta(t)$ and $v_\beta(t)$ will later be used directly in performing the backprojection step. In addition, the angle $\gamma$ (FIG. 9) may also be expressed in terms of the detector coordinates u and v.

To do so, we note that Eq. (3) dictates that:

$$\cos\gamma = \hat{\beta}\cdot\hat{r}. \quad (12)$$

Note that, in the local coordinate system, if the angle $\phi$ is fixed, the vector $\hat{r}$ is confined to the "critical fan" within the plane $\Pi(\vec{x},t;\phi)$ shown in FIG. 9. In other words, the point (u,v) where the ray vector $\hat{r}$ is incident on the detector traverses the filtering line. In the detector plane, the slope of the filtering line is denoted as $\kappa(\vec{x},t)$:

$$\kappa(\vec{x},t) = \frac{v - v_\beta(t)}{u - u_\beta(t)}. \quad (13)$$

Note that the $\vec{x}$ and t dependence in $\kappa$ originates from the $\vec{x}$ and t dependence in $u_\beta(t)$ and $v_\beta(t)$. Therefore, one can see that the same filtering line may be used for the reconstruction of any image point lying in the critical plane $\Pi(\vec{x},t;\phi)$.

Finally we may re-express the filtering kernel in terms of the detector coordinates introduced above. Thus, using Eqs. (11)–(13), we obtain:

$$\frac{d\gamma}{\sin\gamma} = \frac{1}{|\sin\alpha\cos(\beta-t)|}\frac{1}{\sqrt{D^2+u^2+v^2}}\frac{du}{u-u_\beta}, \quad (14)$$

where v satisfies Eq. (13), (i.e. the point lies on the filtering line).

Finally, substituting Eqs. (11) and (14) into Eq. (4), the following reconstruction formula is obtained:

$$f(\vec{x}) = -\frac{1}{4\pi^2}\sum_m\int dt\frac{c_m(\vec{x},t)}{L(\vec{x},t)}q_m[u_\beta(t),v_\beta(t);t], \quad (15)$$

where $$L(\vec{x},t) = \frac{D}{2} - x\cos t - y\sin t, \quad (16)$$

$$q_m[\bar{u},\bar{v};t] = \int_{-\infty}^{+\infty}\int_{-\infty}^{+\infty}du\,dv\delta[v-\bar{v}-\kappa_m(u-\bar{u})]h_H(u-\bar{u})\bar{g}(u,v,t),$$

$$\bar{g}(u,v,t) = \frac{D}{\sqrt{D^2+u^2+v^2}}\left(\frac{D^2+u^2}{D}\frac{\partial}{\partial u} + \frac{uv}{D}\frac{\partial}{\partial v} - \frac{\partial}{\partial t}\right)g(u,v,t),$$

where $$h_H(x) = \frac{1}{x}$$

is the kernel of Hilbert filter, and $\kappa_m$ is the slope of the filtering line in the detector plane.

Figure 10A:
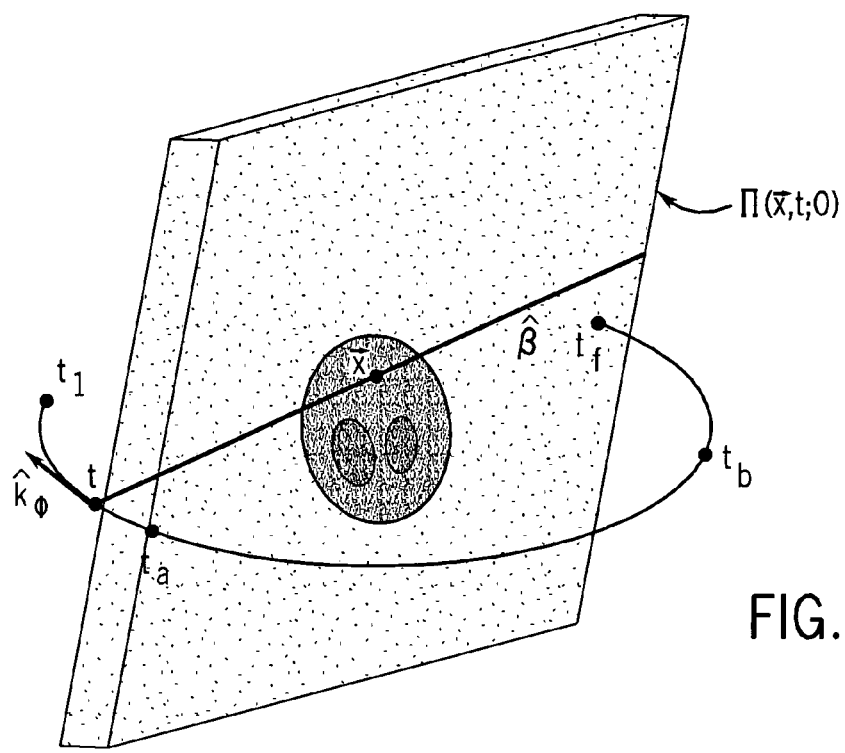
FIGS. 10a, 10b, 10c and 10d are pictorial representations of parameters used to derive equations for the present invention.
Figure 10B:
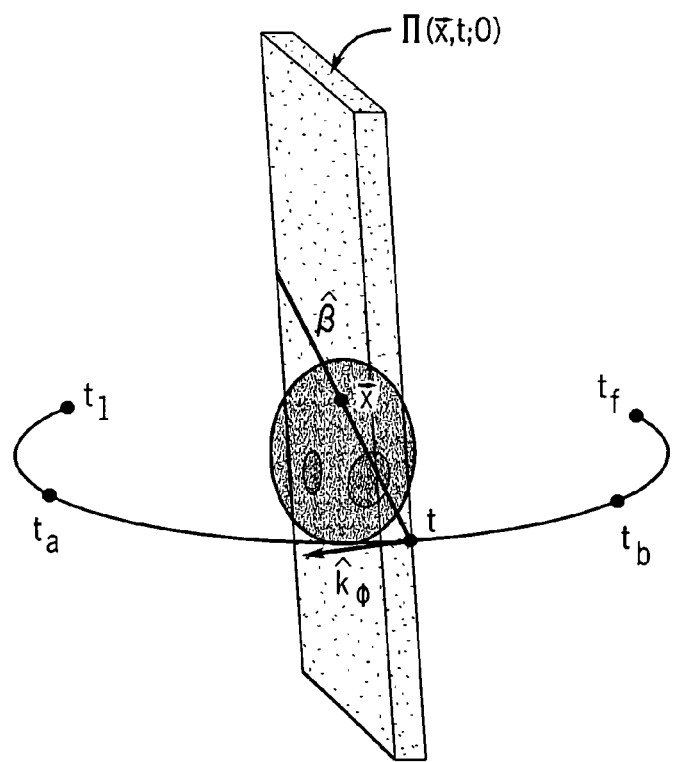
Figure 10C:
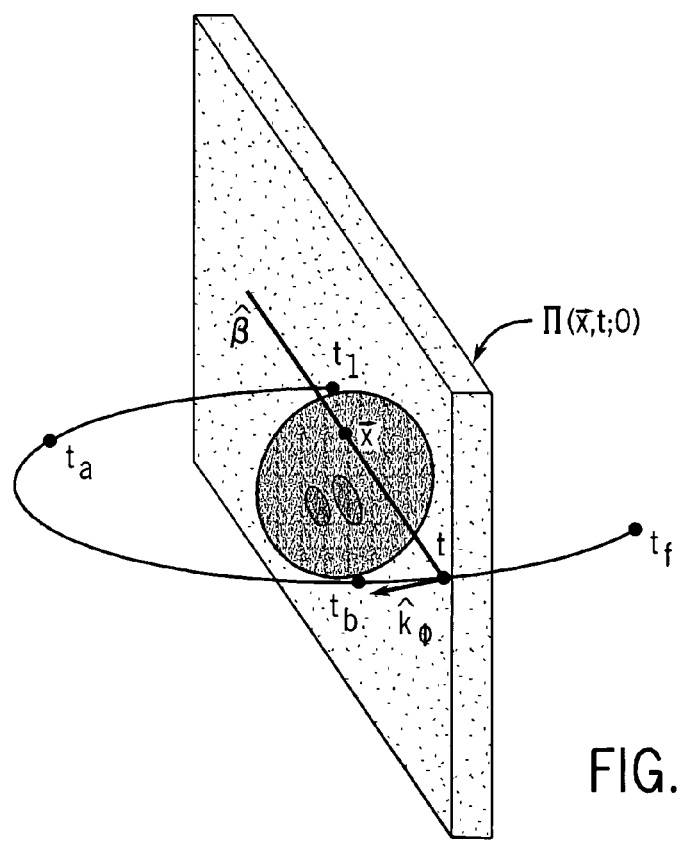
Figure 10D:
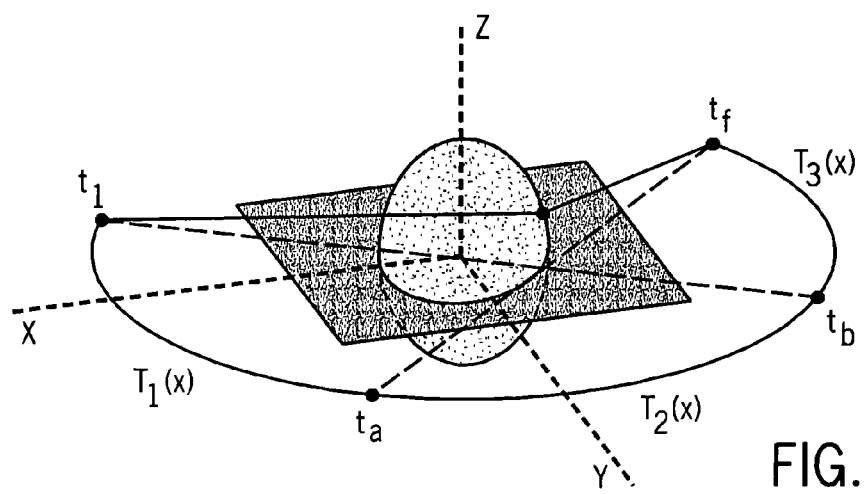

In applying the Katsevich-type cone beam reconstruction formula described above a key task is to calculate the structure factor for the specific arc geometry. Namely, for each given reconstruction point $\vec{x}$ and source point t one must find and weight the critical planes. From Eq. 7 the weighting function is piecewise constant with respect to $\phi$. In order to calculate the structure factor one must find the transition points where the weighting function changes as the plane $\Pi(\vec{x},t;\phi)$ rotates about $\hat{\beta}$. In order to facilitate the analysis, one divides the source trajectory into several different regions based on the number of intersection points between the plane $\Pi(\vec{x},t;0)$ (the plane that is perpendicular to the scanning plane) and the source trajectory as shown in FIGS. 10a–10c. For each image point the source trajectory may be segmented into three regions $T_1$, ($t\in[t_i,t_a]$), $T_2$, ($t\in(t_a,t_b)$) an $T_3$, ($t\in[t_b,t_f]$). The values $t_a$ and $t_b$ are easily determined analytically by projecting the image point to the x-y plane, and then respectively drawing lines from $t_f$ and $t_i$ through the projected image point as shown in FIG. 10d. The intersection between these lines and the source trajectory define $t_a$ and $t_b$, and are used to segment the source trajectory into $T_1$, $T_2$, and $T_3$ as given below in Eq. 20.

The three sets $T_1(\vec{x})$, $T_2(\vec{x})$ and $T_3(\vec{x})$ are defined as:

$$T_1 = (\vec{x})\{t\mid t_i \leq t \leq t_a(\vec{x})\}, \quad (17)$$

$$T_2 = (\vec{x})\{t\mid t_a(\vec{x}) < t < t_b(\vec{x})\}, \quad (18)$$

-continued $$T_3 = (\vec{x})\{t \mid t_b(\vec{x}) \le t \le t_f\}, \quad (19)$$

where $$t_n = \left[t_m + \pi - 2\tan^{-1}\left(\frac{-x\sin t_m + y\cos t_m}{R - x\cos t_m - y\sin t_m}\right)\right] \mod 2\pi, \quad (20)$$

where n=a, b corresponding to m=i, f respectively and R is the gantry radius.

Figure 11A:
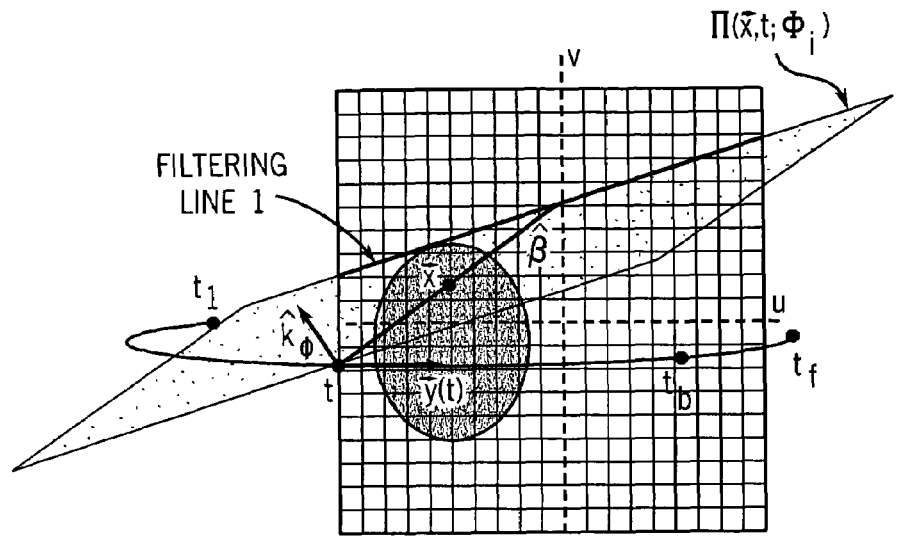
FIGS. 11a, 11b, and 11c are pictorial representations of parameters used to derive equations for the present invention.
Figure 11B:
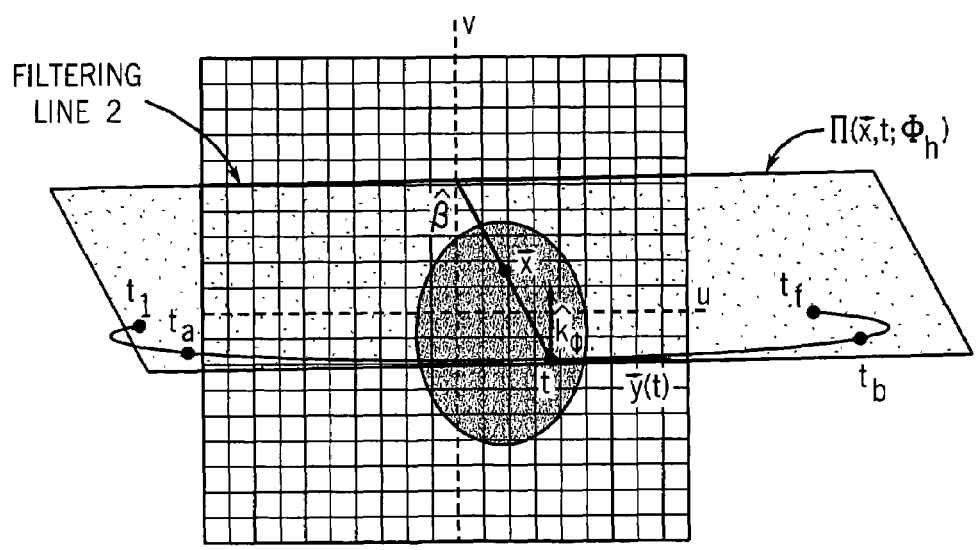
Figure 11C:
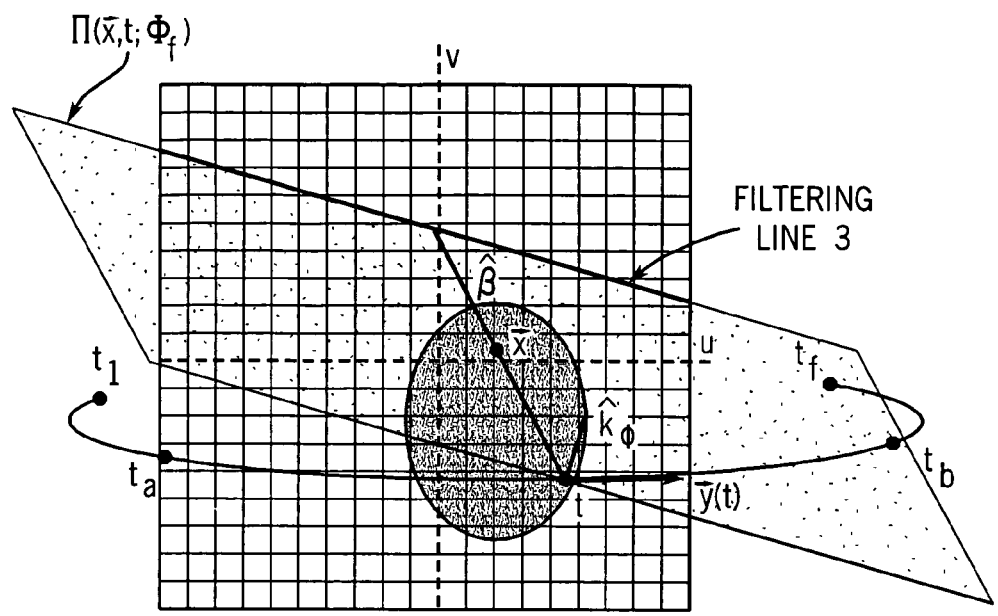

It is important to know the manner in which the weighting function changes for a given image point and a given source point as the plane $\Pi(\vec{x},t;\phi)$ rotates about $\hat{\beta}$. As this plane rotates about $\hat{\beta}$ there are three critical angles where the weighting function abruptly changes. These three examples are illustrated for a sample image point $\vec{x}$ and a sample source point $t\epsilon T_2$ in FIG. 11. The first transition occurs when the plane $\Pi(\vec{x},t;\phi)$ contains $\vec{y}(t_i)$ and thus this critical angle will be referred to as $\phi$. In this case there is a transition from N=1 (before the plane $\Pi(\vec{x},t;\phi)$ reaches $\vec{y}(t_i)$) to N=2 (after the plane $\Pi(\vec{x},t;\phi)$ passes $\vec{y}(t_i)$, therefore the weighting function has a transition from 1 to ½ as shown in FIG. 11a. The second transition occurs at the critical angle when the plane $\Pi(\vec{x},t;\phi)$ is tangential to the source trajectory and thus there is an abrupt jump from N=2 to N=1 and back to N=1 as shown in FIG. 11b. When this transition occurs the associated filtering line is horizontal and thus this critical angle will be referred to as $\phi_h$. The final case shown in FIG. 11c is similar to the first case. Namely, the critical angle occurs when the plane $\Pi(\vec{x},t;\phi)$ contains $\vec{y}(t_f)$ as there is an abrupt transition from N=2 to N=1. It is clear that the discontinuities will be similar for source points in $T_1$ and $T_3$; namely, due to transitions as the plane $\Pi(\vec{x},t;\phi)$ intersects either of the end points or becomes tangential to the source trajectory. To summarize, for all view angles there will be an abrupt jump in the weighting function when $\phi=\phi_m$, m=h, i, f.

In order to calculate the structure factor we need to consider $\text{sgn}[\hat{k}_\phi \cdot \vec{y}(t)]$. The argument of this function is calculated to be:

$$\hat{k}_\phi \cdot \vec{y}(t) = r[\cos\phi\cos(\beta - t) - \sin\phi\cos\alpha\sin(\beta - t)] \quad (21)$$

$$= r\sqrt{\cos^2(\beta - t) + \cos^2\alpha\sin^2(\beta - t)} \sin(\phi - \phi_n).$$

Then we have:

$$\text{sgn}[\hat{k}_\phi \cdot \vec{y}(t)] = \begin{cases} -1, & \text{if } \phi \in [0, \phi_h), \\ 1, & \text{if } \phi \in (0, \pi]. \end{cases} \quad (22)$$

Using the definition of the structure factor and the results in the preceding subsections, for $z \ne 0$ one may obtain:

$$c_h = 1, \quad (23)$$

$$c_i = \begin{cases} -\dfrac{1}{2}, & \text{if } t \in T_3(\vec{x}), \\ \dfrac{1}{2} & \text{if } t \in T_1(\vec{x}) \cup T_2(\vec{x}), \end{cases}$$

$$c_f = \begin{cases} -\dfrac{1}{2}, & \text{if } t \in T_1(\vec{x}), \\ \dfrac{1}{2} & \text{if } t \in T_2(\vec{x}) \cup T_3(\vec{x}), \end{cases}$$

and for $z = 0$:

$$c = \begin{cases} 2, & \text{if } t \in T_2(\vec{x}), \\ 1 & \text{if } t \in T_1(\vec{x}) \cup T_3(\vec{x}). \end{cases} \quad (24)$$

After substituting (23) into (24), we obtain the image reconstruction formula for an arc scanning path:

$$-4\pi^2 f(\vec{x}) = \int_{t_i}^{t_f} dt \frac{1}{L(\vec{x}, t)} q_h[u_\beta(t), v_\beta(t); t] + \quad (25)$$

$$\frac{1}{2}\left(\int_{t_i}^{t_b} - \int_{t_b}^{t_f}\right) dt \frac{1}{L(\vec{x}, t)} q_f[u_\beta(t), v_\beta(t); t] -$$

$$\frac{1}{2}\left(\int_{t_i}^{t_a} - \int_{t_a}^{t_f}\right) dt \frac{1}{L(\vec{x}, t)} q_f[u_\beta(t), v_\beta(t); t],$$

where $t_a$, $t_b$ are shown in FIG. 10d and filter functions $q_h$, $q_i$ and $q_f$ were defined in Eq. 16 The expression for the slopes $\kappa$ used in the filtering process are given below, $$\kappa_h = 0, \quad \kappa_m(\bar{u}, \bar{v}; t) = \frac{\bar{v}}{\bar{u} - D\cot\left(\dfrac{t - t_m}{2}\right)}, \quad m = i, f. \quad (26)$$

To implement the preferred embodiment of the invention we rewrite the reconstruction formula (Eq. 25) into a more convenient form:

$$-4\pi^2 f(\vec{x}) = \int_{t_i}^{t_a} dt \frac{1}{L(\vec{x}, t)} Q_1[\bar{u} = u_\beta(t), \bar{v}_b = v_\beta(t), t] + \quad (27)$$

$$\int_{t_a}^{t_b} dt \frac{1}{L(\vec{x}, t)} Q_2[\bar{u} = u_\beta(t), \bar{v}_b = v_\beta(t), t] +$$

$$\int_{t_b}^{t_f} dt \frac{1}{L(\vec{x}, t)} Q_3[\bar{u} = u_\beta(t), \bar{v}_b = v_\beta(t); t],$$

where

-continued $$q_h(\bar{u}, \bar{v}, t) = \int_{-\infty}^{+\infty} du h_H(u - \bar{u}) \bar{g}[u, \bar{v}, t], \quad (28)$$

$$q_m(\bar{u}, v_m, t) = \int_{-\infty}^{+\infty} du h_H(u - \bar{u}) \bar{g}[u, v_m, t],$$

$$Q_1(\bar{u}, \bar{v}, t) = q_h(\bar{u}, \bar{v}, t) + \frac{1}{2} q_i(\bar{u}, v_i, t) - \frac{1}{2} q_f(u, v_f, t),$$

$$Q_2(\bar{u}, \bar{v}, t) = q_h(\bar{u}, \bar{v}, t) + \frac{1}{2} q_i(\bar{u}, v_i, t) - \frac{1}{2} q_f(u, v_f, t),$$

$$Q_3(\bar{u}, \bar{v}, t) = q_h(\bar{u}, \bar{v}, t) - \frac{1}{2} q_i(\bar{u}, v_i, t) + \frac{1}{2} q_f(u, v_f, t),$$

where $v_m$ is given by $$v_m = \frac{\bar{v}}{\bar{u} - D\cot\left(\frac{t - t_m}{2}\right)} \left[u - D\cot\left(\frac{t - t_m}{2}\right)\right], \, m = i, f. \quad (29)$$

In the implementation of this reconstruction formula it is important to note that the $\vec{x}$ dependence of $Q_m$ (m=1,2, or 3) in Eq. 25 (or Eq. 27) may be expressed directly in terms of detector coordinates $u_\beta(t)$ and $v_\beta(t)$. Thus, the filtering operation is not explicitly voxel dependent, and this reconstruction formula may be implemented in a manner similar to the standard FDK method. For the full-scan case in which the x-ray source and detector array revolve completely around the subject, the filtering direction is identical to the FDK method and in the case of a short and super-short scan there are three separate filtering directions, linear combinations of which makeup three separate sets of filtration data to be backprojected.

The reconstruction steps are summarized below:

Step 1: Modify the cone-beam data by computing the weighted derivative of the measured cone-beam data, $$\bar{g}(u, v, t) = \frac{D}{\sqrt{D^2 + u^2 + v^2}} \left( \frac{D^2 + u^2}{D} \frac{\partial}{\partial u} + \frac{uv}{D} \frac{\partial}{\partial v} - \frac{\partial}{\partial t} \right) g(u, v, t).$$

Step 2: Compute the 1D Hilbert filter of the modified cone-beam data to obtain $Q_1$, $Q_2$, $Q_3$ according to Eq. 28.
Step 3: backproject $Q_1$, $Q_2$, $Q_3$ according to Eq. 27 to obtain $f(\vec{x})$ for each point $\vec{x}$.

DESCRIPTION OF THE PREFERRED EMBODIMENT

Figure 1:
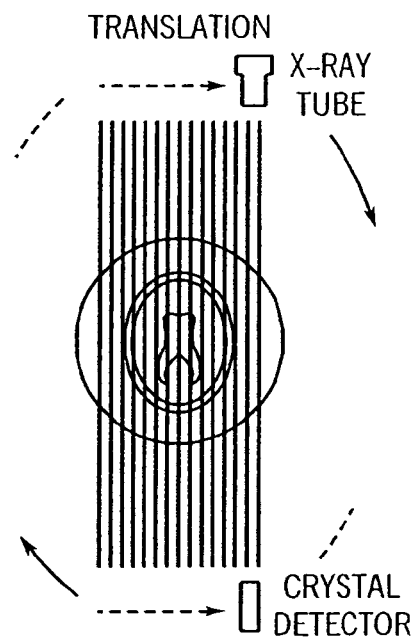
FIGS. 1–4 are schematic representations of different CT system geometries.
Figure 2:
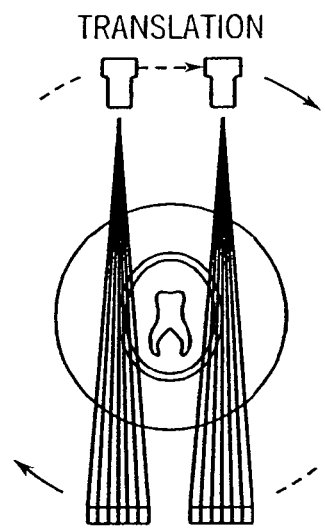
Figure 3:
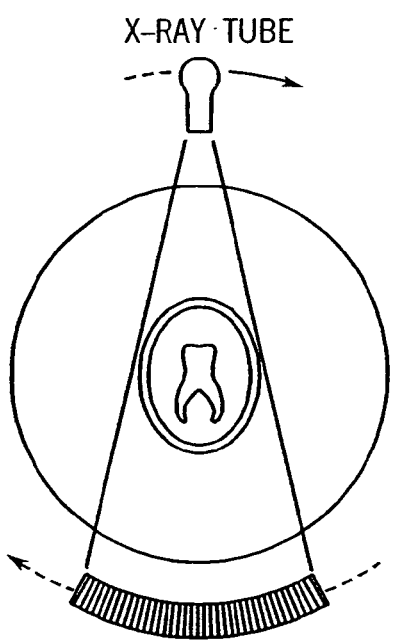
Figure 4:
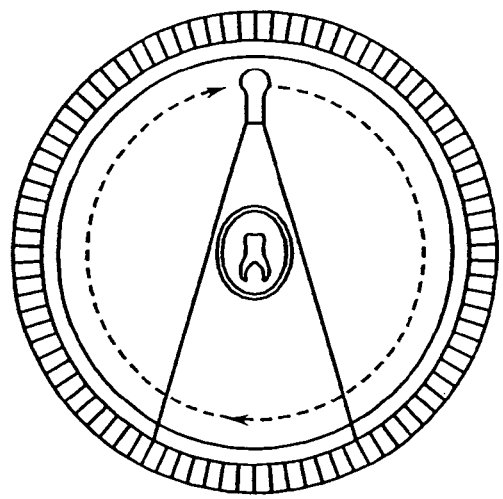
Figure 5:
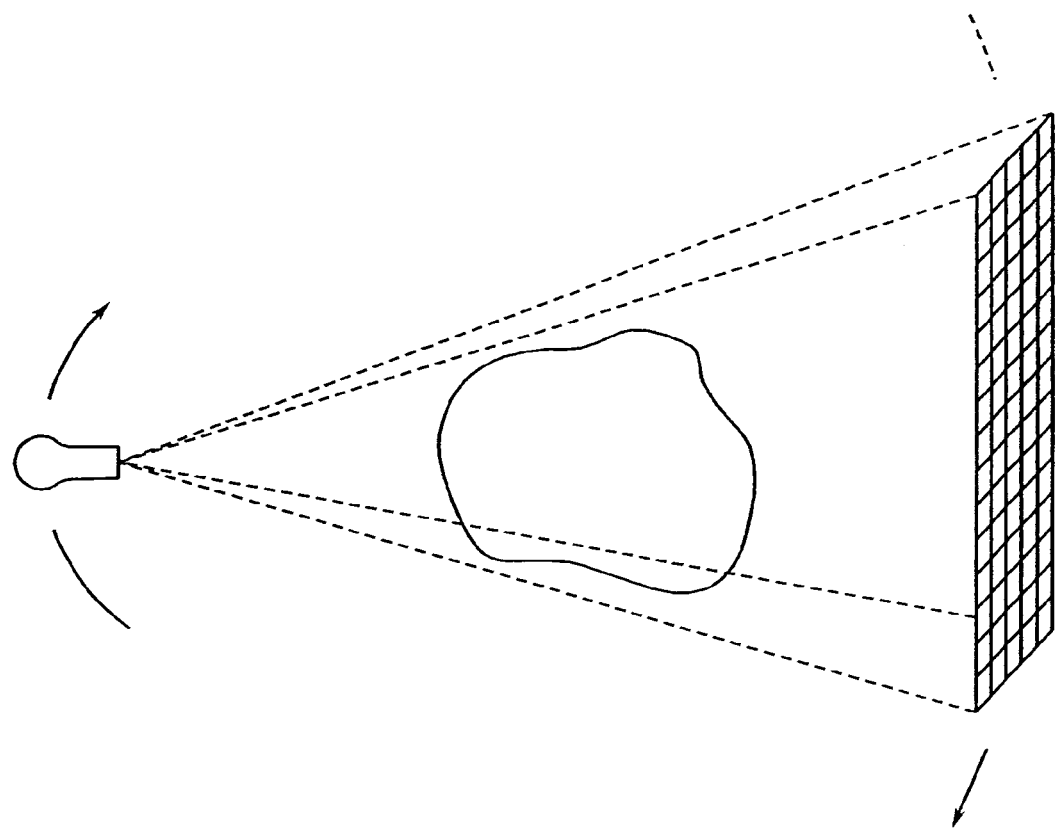
FIG. 5 is a pictorial representation of a 3D, or volume, CT system.
Figure 6:
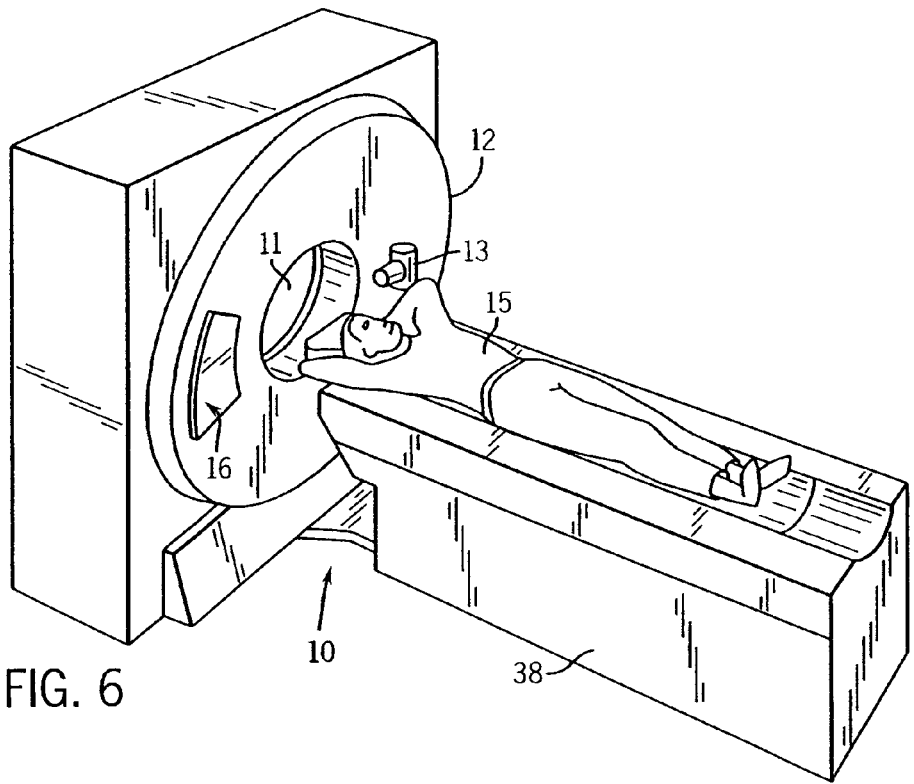
FIG. 6 is a pictorial view of a CT system which employs the present invention.
Figure 7:
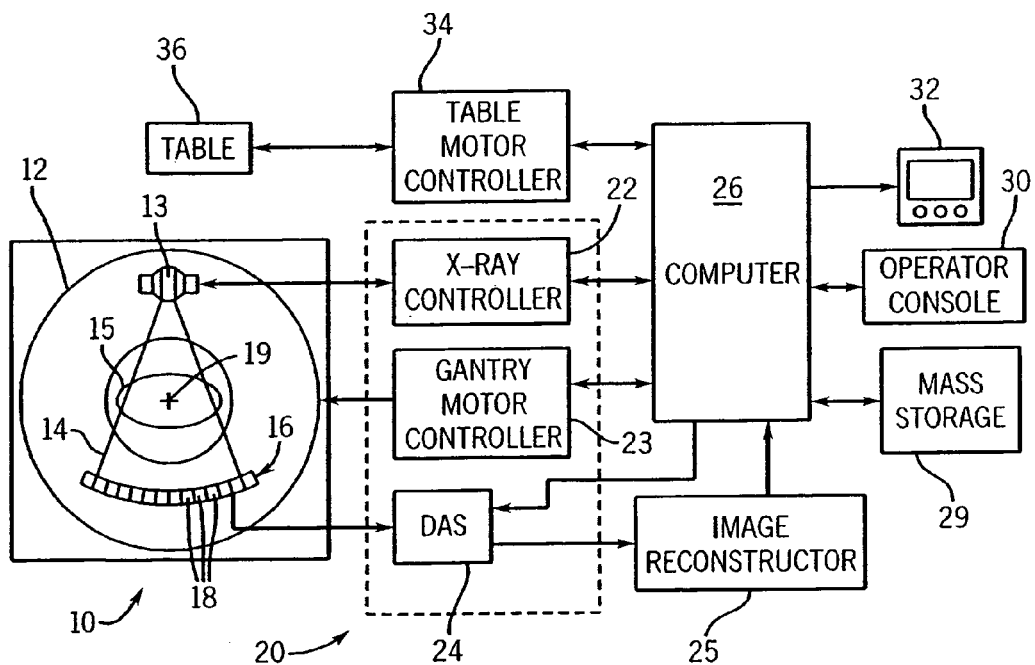
FIG. 7 is a block diagram of the CT system of FIG. 6.

With initial reference to FIGS. 6 and 7, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15. The path y(t) of the x-ray source 13 is thus a circular arc.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

The above-described CT system is designed to rapidly perform a full-scan in which the x-ray source revolves in a circular arc completely around the subject being imaged. The present invention may be employed in such a CT system, but because the invention may also be employed in short-scans and super-short-scans, it is particularly useful when used with a C-arm x-ray system depicted in FIG. 14.

Figure 14:
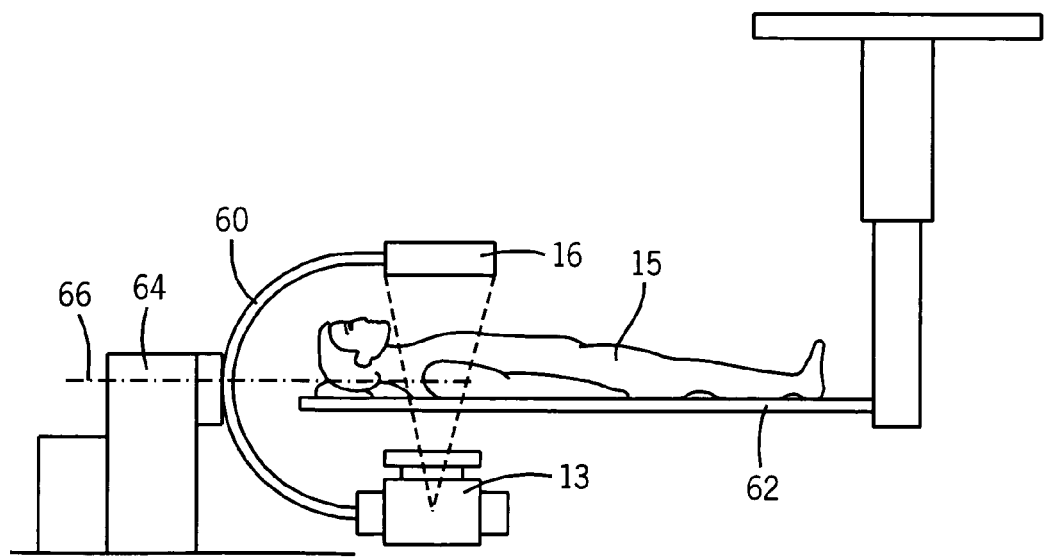
FIG. 14 is a side elevation view of a C-arm x-ray system which employs the present invention.

Referring particularly to FIG. 14, the C-arm x-ray system includes a C-arm 60 to which the two-dimensional detector 16 and the x-ray source 13 are mounted. Here, again the patient 15 is positioned on a table 62 that extends between the source 13 and the detector 16. The C-arm is rotationally mounted to a base 64, and cone beam data is acquired by rotating the x-ray source 13 and detector 16 around a defined axis 66. C-arm scanners are particularly useful in image-guided interventions and they are characterized by scans in which the x-ray source and detector are rotated over a very short arc.

Figure 12A:
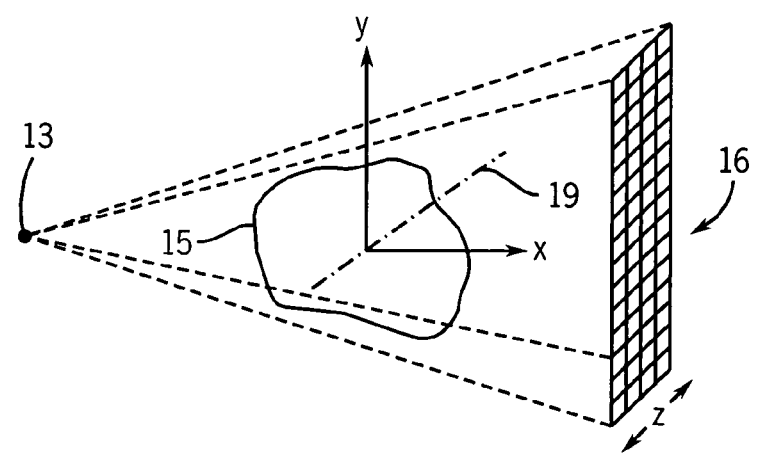
FIGS. 12a and 12b are pictorial representations of the x-ray cone beam and detector array used to acquire data according to the present invention.
Figure 12B:
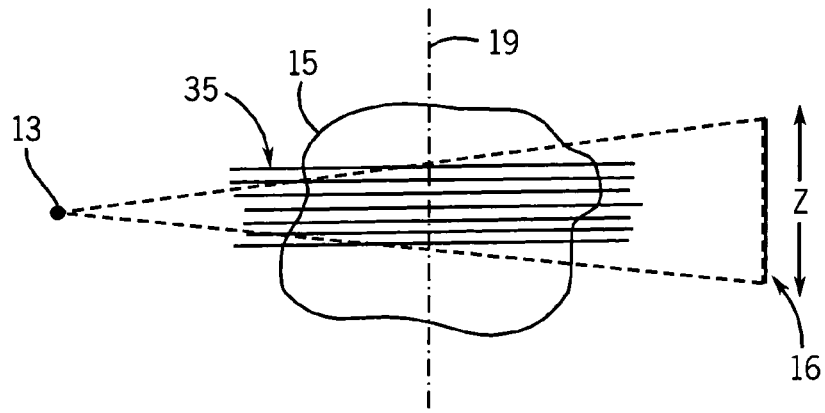

As shown best in FIG. 12a, in the preferred embodiment of the present invention the detector array 16 is a flat array of detector elements 18, having $N_r$ (e.g. 1024) elements 18 disposed along the in-plane (x,y) direction, and $N_z$ (e.g. 1024) elements 18 disposed along the z axis. The x-ray beam emanates from the x-ray source 13 and fans out as it passes through the patient 15 and intercepts the detection array 16. Each acquired view is a $N_r$ by $N_z$ array of attenuation measurements as seen when the gantry is oriented in one of its positions during the scan. As shown in FIG. 12B, the object of the present invention is to reconstruct a set of 2D image slices 35 from the 3D array of acquired data produced by the x-ray cone beam during the scan.

It can be seen that because the cone beam diverges as it passes through the patient 15, the accurate reconstruction of the parallel image slices 35 is not possible with a straight forward fan beam filtering and backprojection process. The present invention enables an accurate reconstruction of the image slices 35 from this acquired cone beam data. In addition, the present invention enables the accurate reconstruction of image slices 35 even when the circular path of the x-ray source 13 is less than a complete circle.

Figure 13:
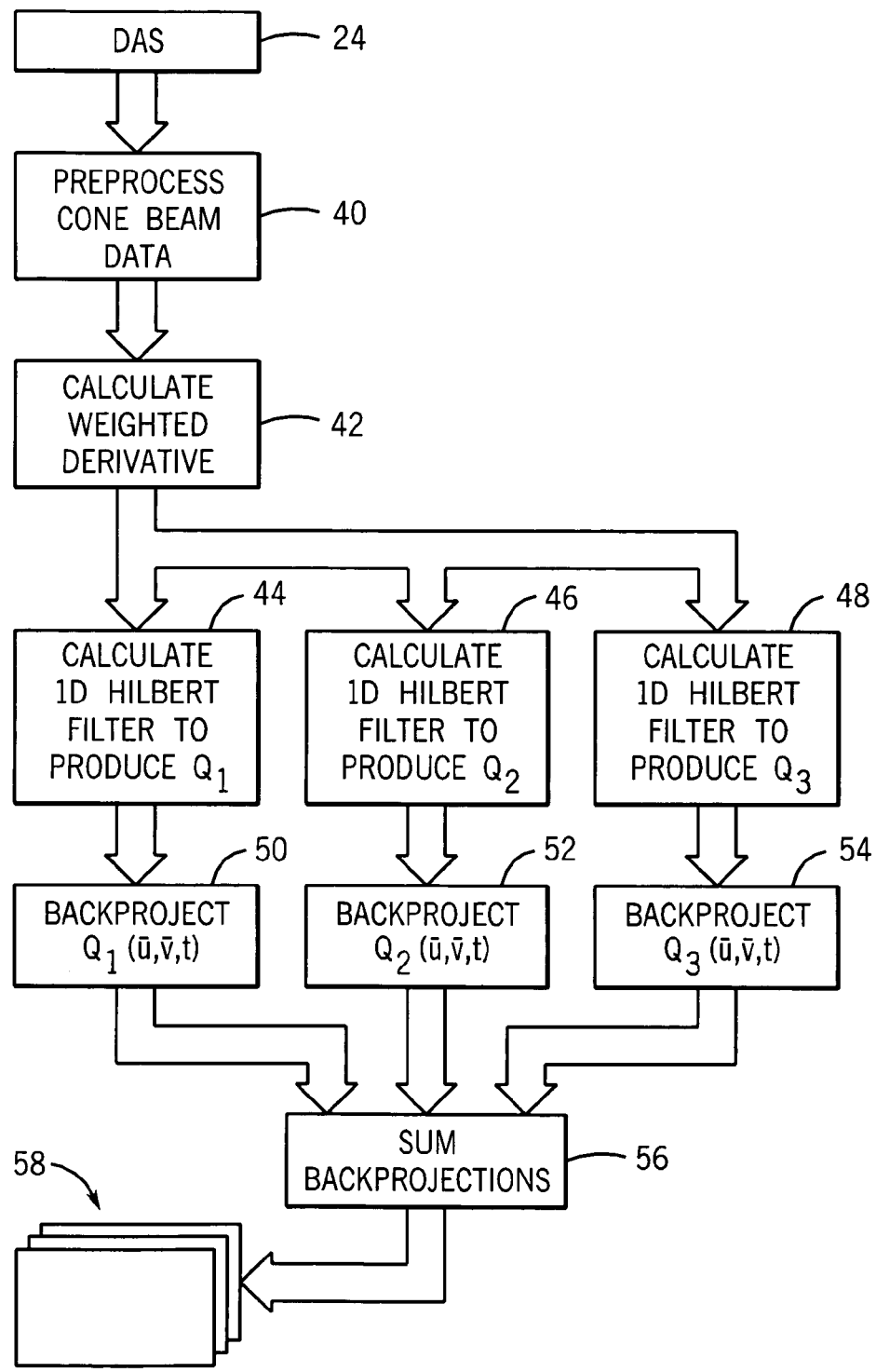
FIG. 13 is a flow chart which illustrates the processing steps in a preferred embodiment of the present invention.

This reconstruction method is implemented in the image reconstructor 25. Referring particularly to FIG. 13, the cone beam projection data is received from the DAS 24 as a two-dimensional array of values which are preprocessed in the standard manner at process block 40. Such preprocessing includes correcting for known errors and offsets and calculating the minus log of the data to convert it to x-ray attenuation values. The preprocessed cone beam attenuation profiles g(u,v,t) are then modified by calculating the weighted derivative ḡ(u,v,t) as indicated at process block 42. This is performed as set forth above in Eq. (16). The 1D Hilbert filter of the weighted derivative of the cone beam data ḡ(u,v,t) is then computed as set forth above in Eq. (28) to produce filtered cone beam data sets $Q_1(\bar{u},\bar{v},t)$, $Q_2(\bar{u},\bar{v},t)$ and $Q_3(\bar{u},\bar{v},t)$ as indicated at process blocks 44, 46 and 48. As indicated by process blocks 50, 52 and 54 these filtered cone beam data sets $Q_1(\bar{u},\bar{v},t)$, $Q_2(\bar{u},\bar{v},t)$ and $Q_3(\bar{u},\bar{v},t)$ are each backprojected as set forth above in Eq. (27) and the backprojected data is summed as indicated at process block 56 to produce a 3D image f(x). The desired 2D image slices 58 are produced from the 3D image and output to computer 26.

The present invention is valid when the x-ray source arc covers an angular range of 180°+ fan angle, namely a short scan mode. The backprojection segments $T_1$, $T_2$, $T_3$ is correspondingly changed for each image voxel. The present invention is also valid even if the source arc is shorter than 180°+ fan angle. This is a super-short scan mode.

A number of variations are possible from the preferred embodiment described above. The differentiations in pre-weighted data may be computed using a fast Fourier transform (FFT) method. Also, the Hilbert convolution process may be implemented using an FFT method. Parameters such as source to detector distance, source to isocenter distance, the source to image point distance may be measured in a geometrical calibration process and incorporate into the method. The convolution process may be implemented using either a horizontal detector coordinate or vertical coordinate. The convolution procedure may be numerically implemented by combining the convolution procedure in terms of horizontal coordinate and in terms of vertical coordinate. The present invention may be applied to a curved detector and circular source trajectory.

It should be apparent to those skilled in the art that the convolution procedure may be numerically implemented by combining the convolution procedure in terms of horizontal coordinate and in terms of vertical coordinate. The present invention may also be applied to a curved detector and circular source trajectory. The present invention may be utilized to reconstruct an image for other clinical applications such as radiation therapy where an x-ray source and a flat-panel imager slowly rotates around the patient. While the invention is most advantageously applied to cone beam data sets, the present invention may also be utilized to reconstruct fan-beam CT images. This is the case of Nz=1.

The invention claimed is:

1. A computed tomography imaging system which comprises:
   a two-dimensional array of detector elements for receiving photons emanating in a cone beam from a source;
   a digital acquisition system for acquiring two-dimensional arrays of cone beam data from the array of detector elements at a series of views in which the source revolves around a subject to be imaged;
   means for calculating a weighted derivative of the acquired cone beam data;
   a first filter coupled to receive the weighted derivative and produce therefrom first filtered cone beam data $Q_1$;
   a second filter coupled to receive the weighted derivative and produce therefrom second filtered cone beam data $Q_2$;
   a third filter coupled to receive the weighted derivative and produce therefrom third filtered cone beam data $Q_3$;
   means for backprojecting the respective first, second and third filtered cone beam data $Q_1$, $Q_2$ and $Q_3$ to produce backprojected data; and
   means for receiving the backprojected data and summing the backprojected data from the respective first, second and third filtered cone beam data to produce an image of the subject.

2. The system as recited in claim 1 in which the first, second and third filters are Hilbert filters.

3. The system as recited in claim 1 in which the source produces x-rays.

4. The system as recited in claim 1 in which the source revolves around the subject in a circular arc.

5. The system as recited in claim 4 in which the source performs a super short scan as it revolves around the subject.

6. A method for producing an image of a subject with a computed tomography imaging system having a source which emits a cone beam and a two-dimensional array of detector elements that receive the cone beam, the steps comprising:
   a) acquiring a set of cone beam data from the array of detector elements at a series of views in which the source follows a trajectory around the subject;
   b) calculating a weighted derivative of the acquired cone beam data;
   c) producing first filtered cone beam data $Q_1$ from the weighted derivative produced in step b);
   d) producing second filtered cone beam data $Q_2$ from the weighted derivative produced in step b);
   e) producing third filtered cone beam data $Q_3$ from the weighted derivative produced in step b);
   f) reprojecting the first, second and third filtered cone beam data $Q_1$, $Q_2$ and $Q_3$ to produce respective first, second and third reprojected data; and
   g) summing corresponding first, second and third reprojected data values to produce an image of the subject.

7. The method as recited in claim 6 in which steps c), d) and e) are performed with Hilbert filters.

8. The method as recited in claim 6 in which the source emits x-rays.

9. The method as recited in claim 6 in which the source follows a circular arc as it revolves around the subject.

10. The method as recited in claim 9 in which the arc extends less than 360° around the subject to perform a short scan.

11. The method as recited in claim 9 in which the arc extends less than 180° plus the width of the cone beam around the subject to perform a very short scan.

* * * * *